(12) United States Patent
Stössel et al.

(10) Patent No.: US 7,560,554 B2
(45) Date of Patent: Jul. 14, 2009

(54) RHODIUM AND IRIDIUM COMPLEXES

(75) Inventors: Philipp Stössel, Frankfurt (DE); Hubert Spreitzer, Viernheim (DE); Heinrich Becker, Eppstein (DE)

(73) Assignee: Merck Patent GmbH (DE)

( * ) Notice: Subject to any disclaimer, the term of this patent is extended or adjusted under 35 U.S.C. 154(b) by 645 days.

(21) Appl. No.: 10/494,585

(22) PCT Filed: Nov. 7, 2002

(86) PCT No.: PCT/EP02/12416

§ 371 (c)(1),
(2), (4) Date: May 10, 2005

(87) PCT Pub. No.: WO03/040160

PCT Pub. Date: May 15, 2003

(65) Prior Publication Data

US 2005/0176958 A1     Aug. 11, 2005

(30) Foreign Application Priority Data

Nov. 9, 2001    (DE)    ................. 101 55 064

(51) Int. Cl.
   *C07F 15/00*   (2006.01)
   *B32B 15/00*   (2006.01)
(52) U.S. Cl. ................. 546/2; 428/690; 546/4
(58) Field of Classification Search .......... 546/2, 546/4, 10; 428/690
   See application file for complete search history.

(56) References Cited

U.S. PATENT DOCUMENTS

| | | | |
|---|---|---|---|
| 7,125,998 B2 | 10/2006 | Stossel et al. | |
| 2001/0019782 A1 * | 9/2001 | Igarashi et al. | 428/690 |

FOREIGN PATENT DOCUMENTS

| | | |
|---|---|---|
| EP | 1138746 | 5/2004 |
| JP | 2001247859 | 9/2001 |
| JP | 2004531485 | 10/2004 |
| WO | WO 02/068435 A1 | 9/2002 |

OTHER PUBLICATIONS

Baldo, M.A. et al., "Very high-efficiency green organic light-emitting devices based on electrophosphorescence", Applied Physics Letters, 75(1): 4-6 (Jul. 5, 1999).

* cited by examiner

*Primary Examiner*—Charanjit S Aulakh
(74) *Attorney, Agent, or Firm*—Hamilton, Brook, Smith & Reynolds, P.C.

(57) ABSTRACT

The present invention describes novel organometallic compounds that are phosphorescence emitters. Such compounds can be used as active components (=functional materials) in a range of different applications that can be assigned in the broadest sense to the electronics industry.

The compounds according to the invention are described by the formulae (I), (Ia), (II) and (IIa).

20 Claims, No Drawings

RHODIUM AND IRIDIUM COMPLEXES

RELATED APPLICATIONS

This application is the U.S. National Stage of International Application No. PCT/EP02/12416, filed Nov. 7, 2002, and published in German, and claims the benefit of German Application No. 101 55 064.2, filed on Nov. 9, 2001.

Organometallic compounds—especially compounds of $d^8$ metals—will in the near future be used as active components (=functional materials) in a range of different applications that can be assigned in the broadest sense to the electronics industry, as functional components.

Organic electroluminescent devices based on organic components (for a general description of their structure see U.S. Pat. No. 4,539,507 and U.S. Pat. No. 5,151,629) and their individual components, organic light-emitting diodes (OLEDs), have already become established in the marketplace, as can be seen from the car radios having "organic display" obtainable from the Pioneer company. Other such products are shortly to be introduced. Nevertheless, significant improvements are still needed before such displays provide genuine competition for, or even outstrip, the liquid crystal displays (LCD) currently dominating the market.

One development in this connection, which has emerged in the last two years, is the use of organometallic complexes that exhibit phosphoresence instead of fluorescence [M. A. Baldo, S. Lamansky, P. E. Burrows, M. E. Thompson, S. R. Forrest, Applied Physics Letters, 1999, 75, 4-6].

For theoretical spin-statistical reasons, the use of organometallic compounds as phosphorescence emitters allows an up to four-fold energy and performance efficiency. Whether or not this new development will be successful depends to a great extent upon whether suitable device compositions can be found that are able to transfer those advantages (triplet emission=phosphorescence in comparison with singlet emission=fluorescence) also to OLEDs. Essential conditions for practical use that may be mentioned here are, especially, long operative service life, a high degree of stability with respect to thermal stress and a low start-up and operating voltage in order to allow mobile applications.

In addition, there need to be efficient chemical routes to the organometallic compounds in question. Organorhodium and organoiridium compounds are of special interest here. In those cases, especially in view of the cost of rhodium and iridium, it is of crucial importance that an efficient route to corresponding derivatives is made available.

5'-Mono-, 5',5"-di- and 5',5",5'''-tri-formylated tris-orthometallated organorhodium and organoiridium compounds (in accordance with compounds (I) or (II)), to which the present invention relates, are central key building blocks in the production of highly efficient triplet emitters, because the aldehyde function can be converted into a large number of functions with the aid of current methods described in the literature. It is thereby possible not only to incorporate those active, light-emitting centres covalently into a large number of polymers, but also to tailor the optoelectronic properties of those building blocks. For example, here—starting from the mentioned structures—typical —C=C— linkage reactions (e.g. Wittig or Wittig-Horner reactions), or C-hetero atom linkage reactions (e.g. for C=N: imine or Schiff's base formation) are possible in order thus either to functionalise the formylated compounds further or to use them as (co)monomers in the preparation of corresponding polymers.

5'-Mono-, 5',5"-di- and 5',5",5'''-tri-formylated tris-orthometallated organorhodium and organoiridium compounds and processes for their preparation have not been described in the literature hitherto. This is true especially of the formylation of aromatic ligands—bonded to the metal centre—, that is to say formylation at the metal complex. A comparison with the prior art is accordingly not possible. The efficient preparation and availability of such aldehydes as pure substances is of great importance, however, for a variety of electro-optical applications.

It has surprisingly been found that the novel compounds (I) or (II)—according to Scheme 1—starting from the tris-orthometallated organorhodium or organoiridium compounds (III) or (IV) and a formylating agent consisting of a formamide and an inorganic or organic acid halide or a dihaloether and a Lewis acid, with a suitable choice of the stoichiometric ratio of the formylating agent in question relative to the compounds (III) or (IV) as well as a suitable choice of the reaction parameters, such as reaction temperature, reaction medium, concentration and reaction times, are obtained reproducibly in an approximately 70-90% yield, without the use of chromatographic purification methods, in purities of >99% according to NMR or HPLC (see Example 1-4).

The process described above is distinguished especially by three properties:

Firstly, the selective 5'-mono-, 5',5"-di- and 5',5",5'''-tri-formylation is unexpected and not known in this form. It is presumably a result of the activation which the position para to the rhodium or iridium atom undergoes as result of that atom. The unexpectedly high activity of that position with respect to electrophilic substitution, here formylation, is specifically exploited by the use of mild formylating agents.

Secondly, the high conversion rate achieved, which is reflected in the reproducibly very good yields of isolated product, is unexpected and unique to the formylation of orthometallated ligands, bonded to metals of the iron triad.

Thirdly, the resulting compounds, without expensive chromatographic purification, are obtained in very good purities of >99% according to NMR or HPLC. This is essential for use in optoelectronic components, and use as intermediates for the preparation of corresponding compounds.

As described above, the compounds according to the invention have not been described before and are thus novel.

The present invention accordingly relates to compounds (I) and (II) according to Scheme 1.

Scheme 1:

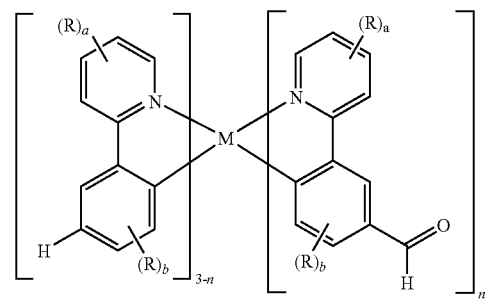

Compounds (I)

Compounds (II)

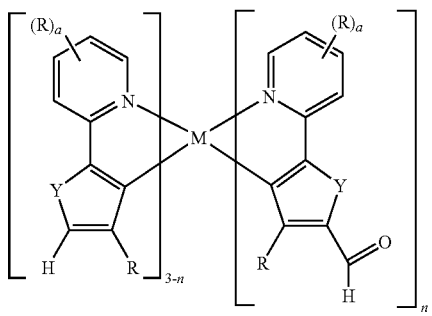

wherein the symbols and indices have the following meanings:

M is Rh, Ir;

Y is O, S, Se;

R is the same or different on each occurrence H, F, Cl, Br, NO$_2$, CN, a straight-chain or branched or cyclic alkyl or alkoxy group having from 1 to 20 carbon atoms, wherein one or more non-adjacent CH$_2$ groups may have been replaced by —O—, —S—, —NR$^1$— or —CONR$^2$— and wherein one or more H atoms may have been replaced by F, or an aryl or heteroaryl group having from 4 to 14 carbon atoms which may be substituted by one or more, non-aromatic radicals R; a plurality of substituents R, both at the same ring and at the two different rings, together may in turn set up a further mono- or poly-cyclic ring system;

R$^1$ and R$^2$ are the same or different H or an aliphatic or aromatic hydrocarbon radical having from 1 to 20 carbon atoms;

a is 0, 1, 2, 3 or 4, preferably 0, 1 or 2;

b is 0, 1, 2 or 3, preferably 0 or 1;

n is 1, 2 or 3.

A further embodiment of the invention comprises those Rh and Ir complexes which have simultaneously ligands of the type as in compounds (I) and those of compounds (II), that is to say mixed ligand systems. They are described by the formulae (Ia) and (IIa):

Compounds (Ia)

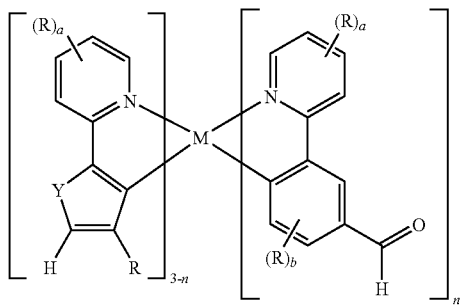

Compounds (IIa)

wherein the symbols and indices have the meanings given under formulae (I) and (II).

The present invention relates also to processes for the preparation of compounds (I) or (II) by reaction of the compounds (III) or (IV), Compounds (III)

Compounds (IV)

wherein M and the radicals and indices Y, R, a and b have the meanings given above, with formulating agents.

The compounds (III) are known, for example, from the application WO 02/060910.

The process according to the invention is illustrated by Scheme 2:

Scheme 2:

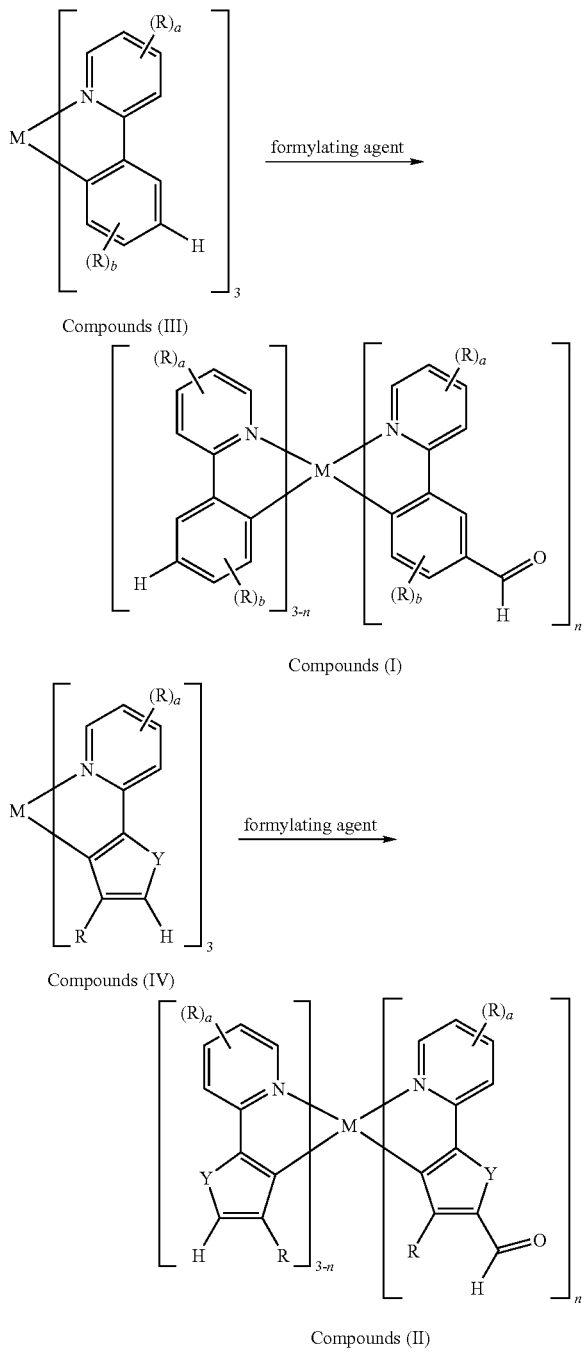

Compounds (III)

Compounds (I)

Compounds (IV)

Compounds (II)

Formylating agents according to the invention are formamides and an inorganic or organic acid halide in a molar ratio of from 1:1 to 100:1, for example N-methyl-formamide (MFA), N,N-dimethyl-formamide (DMF), N-methyl-formanilide in combination with phosphorus oxide trichloride, thionyl chloride, sulphuryl chloride and oxalyl chloride.

Those formulating agents are referred to as formulating agents (1) below. When stoichiometric ratios of such formylating agents (1) relative to other compounds are mentioned, the molar amount of inorganic or organic acid halide in the mixture of formamide and acid halide is the reference basis.

Further formylating agents according to the invention are organic dihalomethyl ethers and Lewis acids in a ratio of from 1:1 to 10:4, for example 1,1-dichloro-methoxy-methane, -ethane, -propane or -butane in combination with titanium (IV) chloride, tin(IV) chloride or aluminium(III) chloride.

Those formylating agents are referred to as formylating agents (2) below.

When stoichiometric ratios of such formylating agents (2) relative to other compounds are mentioned, the molar amount of dihalomethyl ether is the reference basis.

In the process according to the invention, a stoichiometric ratio of the formylating agents (1) or (2) relative to the compounds (III) or (IV) of 1:1 results selectively in the compounds (I) or (II) wherein n=1. This is a surprising and unforeseeable result.

In the process according to the invention, a stoichiometric ratio of the formylating agents (1) or (2) relative to the compounds (III) or (IV) of 2:1 results selectively in the compounds (I) or (II) wherein n=2. This is a surprising and unforeseeable result.

In the process according to the invention, a stoichiometric ratio of the formylating agents (1) or (2) relative to the compounds (III) or (IV) of from 3:1 to 100:1 results selectively in the compounds (I) or (II) wherein n=3. This is a surprising and unforeseeable result.

The stoichiometric ratios described herein are preferred embodiments of the present invention, since they lead to uniformly substituted products. It will be understood that slight departures from the above-mentioned ratios still lead to good to acceptable results.

Reaction media according to the invention, when formylating agents (1) are used, are firstly the formamides themselves, which serve both as constituent of the formylating agent and as reaction medium. Secondly, further co-solvents, such as ethers, e.g. diethyl ether, di-n-butyl ether, methyl tert-butyl ether, tetrahydrofuran or dioxane, halogenated hydrocarbons, such as dichloromethane, chloroform or 1,2-dichloroethane and non-reactive aromatic hydrocarbons, such as chlorobenzene, o-, m- and p-dichlorobenzene or mixtures thereof, toluene, o-, m- and p-xylene or mixtures thereof, can be used.

Reaction media according to the invention, when formylating agents (2) are used, are aprotic solvents, such as dichloromethane, chloroform, 1,2-dichloroethane, 1,1,2,2-tetrachloroethane and carbon disulphide.

According to the invention, the reaction is carried out in a temperature range of from −10° C. to 120° C., preferably from 0° C. to 100° C., more especially from 0° C. to 80° C.

According to the invention, the concentration of rhodium-containing or iridium-containing starting materials—compounds (III) or compounds (IV)—is in the range of from 0.0005 mol/l to 2 mol/l, more especially in the range of from 0.002 mol/l to 0.5 mol/l.

According to the invention, the rhodium-containing or iridium-containing starting materials can be dissolved or suspended in the reaction medium.

According to the invention, the reaction is carried out within a period of from 10 minutes to 100 hours, preferably within a period of from 1 hour to 60 hours.

Using the synthesis methods described herein it is possible to prepare inter alia the examples of compounds (I) and (II) shown below.

Example 1
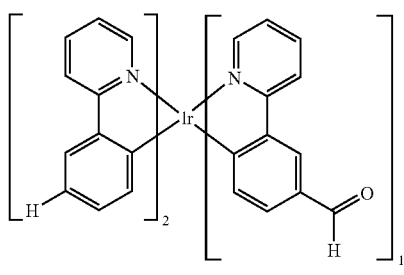
Example 2
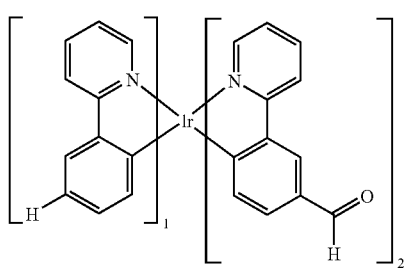
Example 3
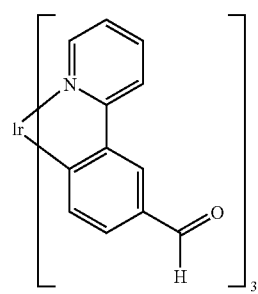
Example 4
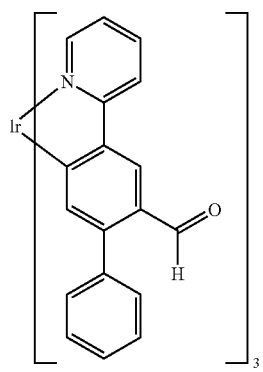
Example 5
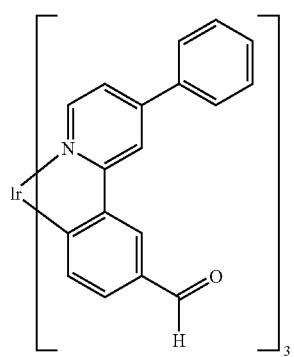
-continued
Example 6
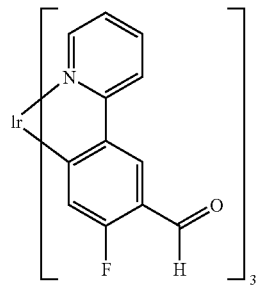
Example 7
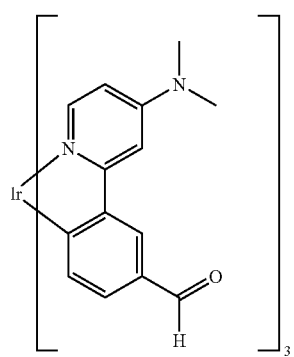
Example 8
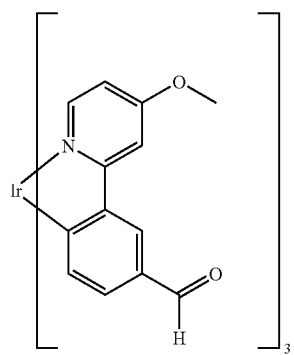
Example 9
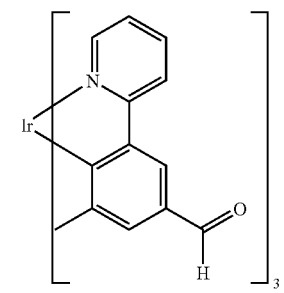
Example 10
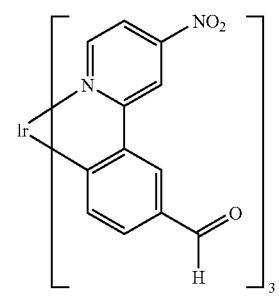

Example 11
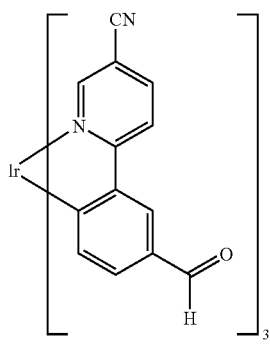
Example 12
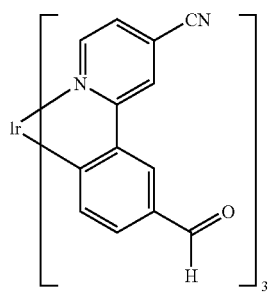
Example 13
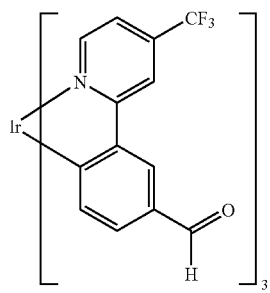
Example 14
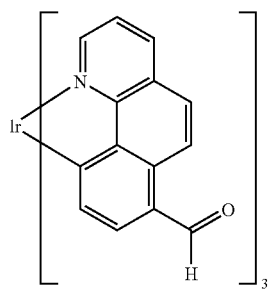
Example 15
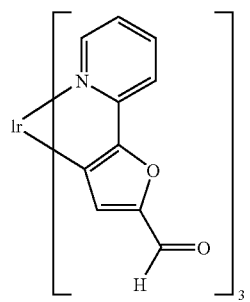
Example 16
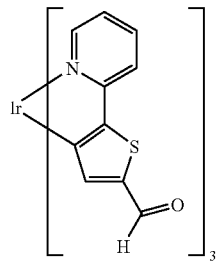
Example 17
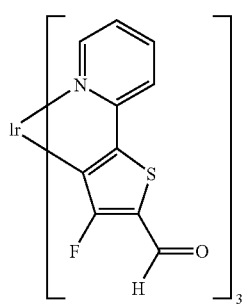
Example 18
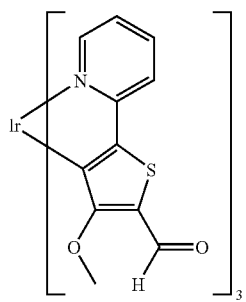
Example 19
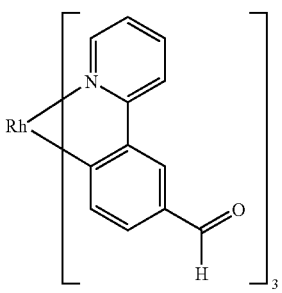
Example 20
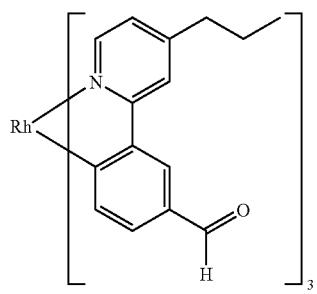

-continued

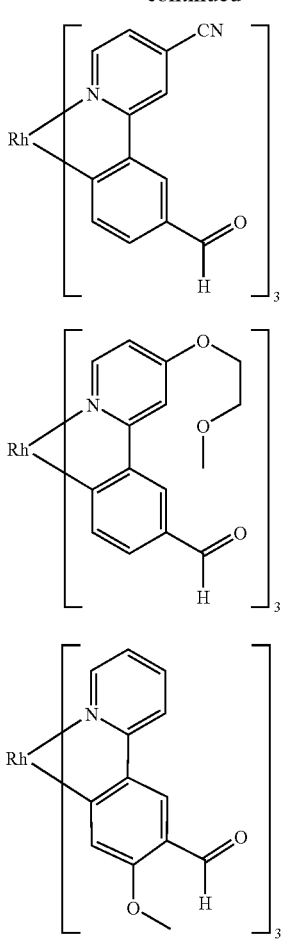

Example 21

Example 22

Example 23

The compounds according to the invention so obtained can then be used, for example, as co-monomers for the production of corresponding conjugated or partially conjugated homo- or co-polymers. They can be incorporated by polymerisation inter alia into soluble polyfluorenes (e.g. according to EP-A-842 208 or WO 00/22026), poly-spirobifluorenes (e.g. according to EP-A-707 020, EP-A-894 107), poly-para-phenylenes (e.g. according to WO 92/18552), poly-carbazoles or polythiophenes (e.g. according to EP-A-1 028 136).

The polyfluorenes disclosed in EP-A-842 208 and WO 00/22026 and their homo- and co-polymers form part of this description.

The poly-spirobifluorenes disclosed in EP-A-707 020 and EP-A-894 107 and their homo- and co-polymers form part of this description.

The poly-para-phenylenes disclosed in WO 92/18552 and their homo- and co-polymers form part of this description.

The polythiophenes disclosed in EP-A-1 028 136 and their homo- and co-polymers form part of this description.

The above-mentioned polymers can be used in electronic components, such as organic light-emitting diodes (OLEDs), organic integrated circuits (O-ICs), organic field effect transistors (OFETs), organic thin-film transistors (OTFTs), organic solar cells (O-SCs), organic laser diodes (O-lasers), organic colour filters for liquid crystal displays or organic photoreceptors.

Furthermore, the compounds according to the invention may of course also be further functionalised by the types of reaction mentioned e.g. in the introduction, and thus reacted to form expanded low molecular weight Rh or Ir complexes. Here there may be mentioned, as an example, the functionalisation with phosphonium salts or phosphonates in accordance with Wittig or Wittig-Horner or with amines, with removal of water, to form imines or Schiff's bases.

The present invention is illustrated in greater detail by the following Examples, but it is not intended to limit the invention thereto. The person skilled in the art will be able to prepare further complexes according to the invention or to apply the process according to the invention on the basis of the descriptions without contributing any inventive activity.

1. Synthesis of Symmetrically and Asymmetrically Formylated Tris-Ortho-Metallated Organorhodium or Organoiridium Compounds:

The following syntheses were—unless otherwise indicated—carried out under a protective gas atmosphere and with the use of dry solvents. The starting materials were obtained from the ALDRICH company [N,N-dimethyl-formamide, phosphorus oxide trichloride, 1,1-dichloromethyl methyl ether, tin(IV) chloride]. fac-Tris[2-(2-pyridinyl-κN) phenyl-κC]-iridium(III) was prepared as described in the application WO 02/060910.

Numbering scheme for the assignment of the $^1$H-NMR signals [according to: C. Coudret, S. Fraysse, J.-P- Launay, Chem. Commun., 1998, 663-664]:

Scheme 3:

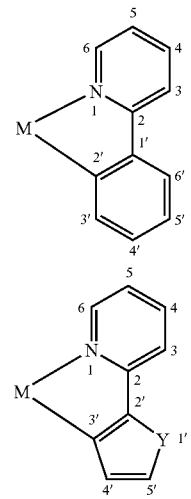

EXAMPLE 1 fac-Bis[2-(2-pyridinyl-κN)phenyl-κC]-[2-(2-pyridinyl-κN)(5-formylphenyl)-κC]-iridium(III)

1.53 g=930 μl (10 mmol) of phosphorus oxide trichloride were added dropwise, with stirring, to 80 ml of N,N-dimethyl-formamide over a period of 5 min. When the addition was complete, the resulting mixture was stirred at room temperature for 1 hour. 6.548 g (10 mmol) of fac-tris[2-(2-pyridinyl-κN)phenyl-κC]-iridium(III) were added to the mixture all at once and the yellow suspension was heated to 80° C. After being stirred at 80° C. for 40 hours, the deep-red solution was allowed to cool to room temperature and poured into 300 ml of aqueous 1 N NaOH. After 1 hour, the yellow mixture was extracted twice with 150 ml of dichloromethane, the combined organic phases were washed three times with 200 ml of water and then dried over magnesium sulphate. After filtration and concentration of the organic phase, the resulting solid was recrystallised twice from toluene/ethanol and finally dried in vacuo (60° C., $10^{-4}$ mbar). The yield—at a purity of >99.5% according to $^1$H-NMR—was 5.74 g-5.92 g corresponding to 84.0-86.7%.

$^1$H-NMR (DMSO-d6): [ppm]=9.78 (s, 1H, C(O)H), 8.13-8.10 (m, 1 H), 8.02-7.99 (m, 2 H), 7.84-7.98 (m, 1 H), 7.61-7.42 (m, 5 H), 7.16-7.14 (m, 1 H), 6.92-6.75 (m, 12 H), 6.68-6.65 (m, 1 H).

EXAMPLE 2 fac-[2-(2-Pyridinyl-κN)phenyl-κC]-bis[2-(2-pyridinyl-κN)(5-formylphenyl)-κC]-iridium(III)

3.07 g=1.86 ml (20 mmol) of phosphorus oxide trichloride were added dropwise, with stirring, to 80 ml of N,N-dimethyl-formamide over a period of 5 min. When the addition was complete, the resulting mixture was stirred at room temperature for 1 hour. 6.548 g (10 mmol) of fac-tris[2-(2-pyridinyl-κN)phenyl-κC]-iridium(III) were added to the mixture all at once and the yellow suspension was heated to 80° C. After being stirred at 80° C. for 40 hours, the deep-red solution was allowed to cool to room temperature and poured into 300 ml of aqueous 1 N NaOH. After 1 hour the yellow mixture was extracted twice with 150 ml of dichloromethane, the combined organic phases were washed three times with 200 ml of water and then dried over magnesium sulphate. After filtration and concentration of the organic phase, the resulting solid was recrystallised twice from toluene/ethanol and dried in vacuo (60° C., $10^4$ mbar). The yield—at a purity of >99.5% according to $^1$H-NMR—was 5.79 g-6.02 g corresponding to 81.4-84.7%.

$^1$H-NMR (DMSO-d6): [ppm]=9.82 (s, 2 H, C(O)H), 8.13-8.10 (m, 2 H), 8.02-7.99 (m, 1 H), 7.84-7.98 (m, 2 H), 7.61-7.42 (m, 3 H), 7.16-7.14 (m, 2 H), 6.92-6.75 (m, 10 H), 6.68-6.65 (m, 2 H).

EXAMPLE 3 fac-Tris[2-(2-pyridinyl-κN)(5-formylphenyl)-κC]-iridium(III)

61.33 g=37.3 ml (400 mmol) of phosphorus oxide trichloride were added dropwise, with stirring and ice-cooling, to 200 ml of N,N-dimethyl-formamide over a period of 30 min. When the addition was complete, the resulting mixture was stirred at room temperature for 1 hour. 6.548 g (10 mmol) of fac-tris[2-(2-pyridinyl-κN)phenyl-κC]-iridium(III) were added to the mixture all at once and the yellow suspension was heated to 80° C. After being stirred at 80° C. for 16 hours, the deep-red solution was allowed to cool to room temperature and poured into a well stirred mixture of 100 ml of ethanol and 800 ml of aqueous 1 N NaOH. After 10 hours, the yellow finely crystalline precipitate was filtered off with suction (P 3), washed five times with 50 ml of water and once with 20 ml of ice-cold ethanol. After recrystallisation twice from toluene/ethanol, the solid was dried in vacuo (60° C., $10^4$ mbar). The yield—at a purity of >99.5% according to $^1$H-NMR—was 5.92 g-6.16 g corresponding to 80.1-83.3%.

$^1$H-NMR (CDCl$_3$): [ppm]=9.87 (s, 3 H, C(O)H), 8.18 (d, 3 H, $^4J_{HH}$=1.7 Hz, H6'), 8.08 (br. dd, 3 H, $^3J_{HH}$=8.4 Hz, $^4J_{HH}$=1.7 Hz, H6), 7.75 (ddd, 3 H, $^3J_{HH}$=8.4 Hz, $^3J_{HH}$=6.6 Hz, $^4J_{HH}$=1.3 Hz, H5), 7.51 (dd, 3 H, $^3J_{HH}$=5.1 Hz, $^4J_{HH}$=1.3 Hz, H3), 7.03 (ddd, 3 H, $^3J_{HH}$=6.6 Hz, $^3J_{HH}$=5.1 Hz, $^4J_{HH}$=1.7 Hz, H4), 7.25 (dd, 3H, $^3J_{HH}$=7.7 Hz, $^4J_{HH}$=1.7 Hz, H4'), 6.98 (d, 3 H, $^3J_{HH}$=7.7 Hz, H3').

EXAMPLE 4 fac-Tris[2-(2-pyridinyl-κN)(5-formylphenyl)-κC]-iridium(III)

60 ml of 1M tin(IV) chloride solution in dichloromethane (60 mmol) and then 3.45 g=2.7 ml (30 mmol) of 1,1-dichloromethyl methyl ether were added dropwise to a suspension, cooled to 0° C., of 6.548 g (10 mmol) of fac-tris[2-(2-pyridinyl-κN)phenyl-κC]-iridium(III) in 500 ml of dichloromethane. The red-brown reaction mixture was allowed to rise to room temperature and stirred for a further 45 min. After hydrolysis by addition of 200 g of ice, the organic phase was separated off, washed three times with 200 ml of saturated sodium hydrogen carbonate solution and dried over magnesium sulphate. After the drying agent had been filtered off and the organic phase concentrated, the yellow solid was recrystallised twice from toluene/ethanol and dried in vacuo (60° C., $10^{-4}$ mbar). The yield—at a purity of >99.0% according to $^1$H-NMR—was 5.51 g-5.78 g corresponding to 74.5-78.2%.

$^1$H-NMR (CDCl$_3$), see Example 3.

The invention claimed is:

1. A compound represented by formulae (I) or (II):

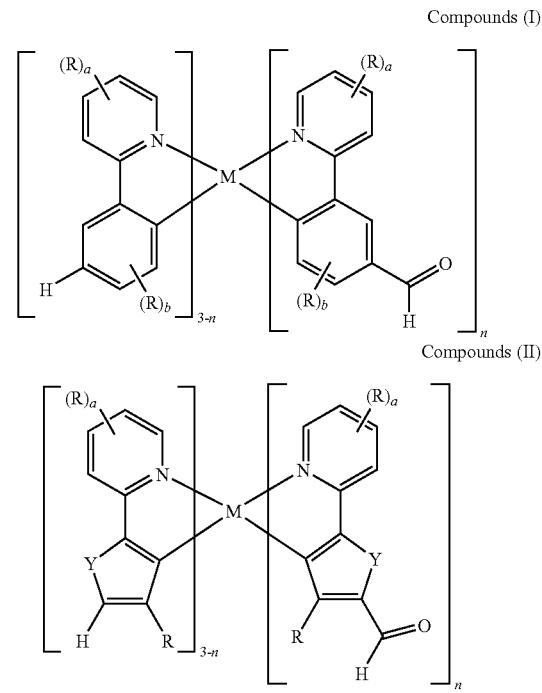

wherein
  M is Rh or Ir;
  Y is the same or different and is O, S, or Se;
  R is the same or different on each occurrence and is H, F, Cl, Br, NO$_2$, CN, or a straight-chain or branched or cyclic alkyl or alkoxy group having 1 to 20 carbon atoms, wherein one or more non-adjacent CH$_2$ groups is optionally replaced by —O—, —S—, —NR$^1$— or —CONR$^2$— and wherein one or more H atoms is optionally replaced by F, or an aryl or heteroaryl group having 4 to 14 carbon atoms which are optionally substituted by one or more non-aromatic radicals R;

$R^1$ and $R^2$ are each the same or different and are H or an aliphatic or aromatic hydrocarbon radical having 1 to 20 carbon atoms;

a is the same or different and is 0, 1, 2, 3, or 4;

b is the same or different and is 0, 1, 2, or 3; and n is 1, 2, or 3.

2. The compound of claim 1, wherein the purity of the compound is greater than 99%.

3. A compound represented by formulae (Ia) or (IIa):

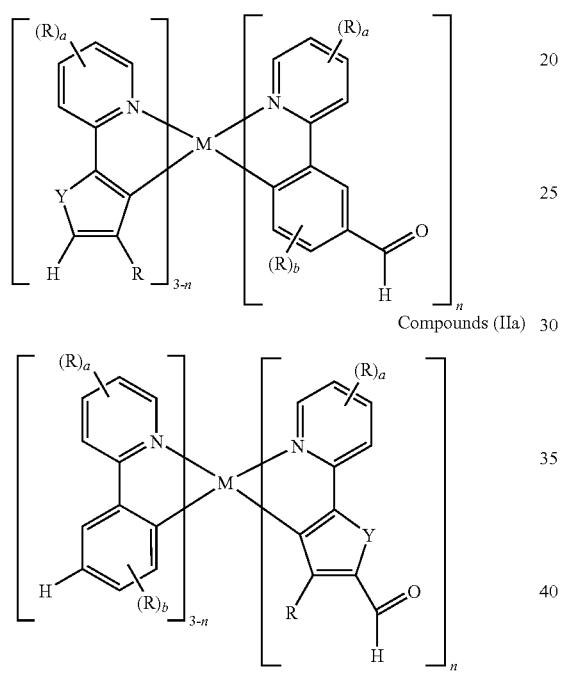

Compounds (Ia)

Compounds (IIa)

wherein

M is Rh or Ir;

Y is the same or different and is O, S, or Se;

R is the same or different on each occurrence and is H, F, Cl, Br, $NO_2$, CN, or a straight-chain or branched or cyclic alkyl or alkoxy group having 1 to 20 carbon atoms, wherein one or more non-adjacent $CH_2$ groups is optionally replaced by —O—, —S—, —$NR^1$— or —$CONR^2$— and wherein one or more H atoms is optionally replaced by F, or an aryl or heteroaryl group having 4 to 14 carbon atoms which are optionally substituted by one or more non-aromatic radicals R;

$R^1$ and $R^2$ are each the same or different and are H or an aliphatic or aromatic hydrocarbon radical having 1 to 20 carbon atoms;

a is the same or different and is 0, 1, 2, 3, or 4;

b is the same or different and is 0, 1, 2, or 3; and n is 1, 2, or 3.

4. The compound of claim 3, wherein the purity of the compound is greater than 99%.

5. A method of preparing a compound represented by formulae (I) or (II):

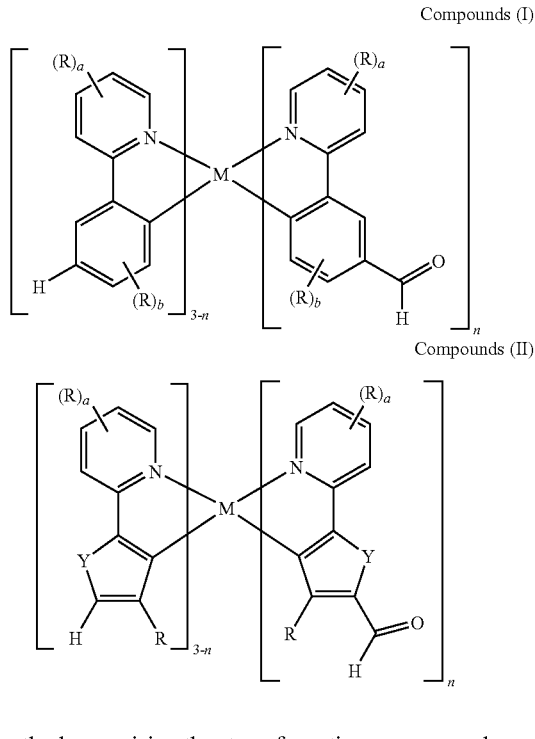

Compounds (I)

Compounds (II)

the method comprising the step of reacting a compound represented by formulae (III) or (IV)

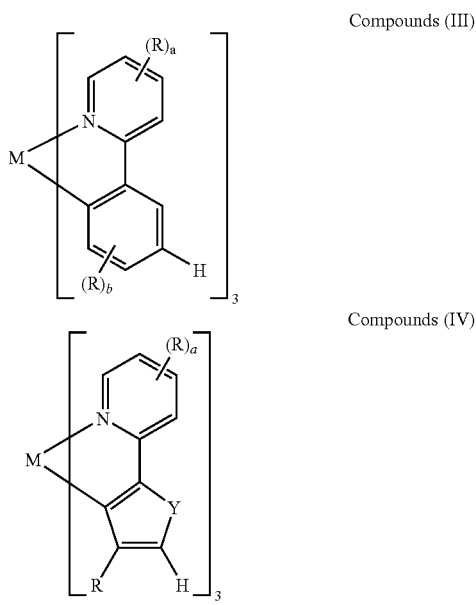

Compounds (III)

Compounds (IV)

with a formylating agent, wherein

M is Rh or Ir;

Y is the same or different and is O, S, or Se;

R is the same or different on each occurrence and is H, F, Cl, Br, $NO_2$, CN, or a straight-chain or branched or cyclic alkyl or alkoxy group having 1 to 20 carbon atoms, wherein one or more non-adjacent $CH_2$ groups is optionally replaced by —O—, —S—, —NR¹— or —CONR²— and wherein one or more H atoms is optionally replaced by F, or an aryl or heteroaryl group having 4 to 14 carbon atoms which are optionally substituted by one or more non-aromatic radicals R;

R¹ and R² are each the same or different and are H or an aliphatic or aromatic hydrocarbon radical having 1 to 20 carbon atoms;

a is the same or different and is 0, 1, 2, 3, or 4;

b is the same or different and is 0, 1, 2, or 3; and n is 1, 2, or 3.

6. The method of claim 5, wherein the formylating agent used is a formamide and an inorganic or organic acid halide in a molar ratio of from 1:1 to 100:1.

7. The method of claim 6, wherein that the formamide used is N-methyl-formamide (MFA), N,N-dimethyl-formamide (DMF), or N-methyl-formanilide.

8. A method of claim 6, wherein the inorganic or organic acid halide used is phosphorus oxide trichloride, thionyl chloride, sulfuryl chloride, or oxalyl chloride.

9. The method of claim 5, wherein the formylating agent used is an organic dihalomethyl ether and a Lewis acid in a molar ratio of from 1:1 to 1:4.

10. The method of claim 9, wherein the dihalomethyl ether used is 1,1 -dichloromethoxy-methane, -ethane, -propane, or -butane.

11. The method of claim 9, wherein the Lewis acid used is titanium(IV) chloride, tin(IV) chloride, or aluminium(III) chloride.

12. The method of claim 5, wherein a stoichiometric ratio of the formylating agent relative to the compound represented by formulae (III) or (IV) of 1:1 is used, and wherein the formylating agent is:

i) a formamide and an inorganic or organic acid halide in a molar ratio of from 1:1 to 100:1, or ii) an organic dihalomethyl ether and Lewis acid in a molar ratio of from 1:1 to 1:4.

13. The method of claim 5, wherein a stoichiometric ratio of the formylating agent relative to the compound represented by formulae (III) or (IV) of 2:1 is used, and wherein the formylating agent is:

i) a formamide and an inorganic or organic acid halide in a molar ratio of from 1:1 to 100:1, or ii) an organic dihalomethyl ether and Lewis acid in a molar ratio of from 1:1 to 1:4.

14. The method of claim 5, wherein a stoichiometric ratio of the formylating agent relative to the compound represented by formulae (III) or (IV) of from 3:1 to 100:1 is used, and wherein the formylating agent is:

i) a formamide and an inorganic or organic acid halide in a molar ratio of from 1:1 to 100:1, or ii) an organic dihalomethyl ether and Lewis acid in a molar ratio of from 1:1to 1:4.

15. A method of manufacturing a conjugated or partially conjugated polymer material, comprising the step of incorporating into a polymer a compound of formulas (I), (II), (Ia), or (IIa):

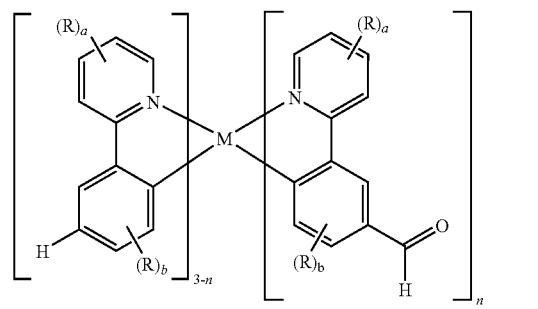
Compounds (I)

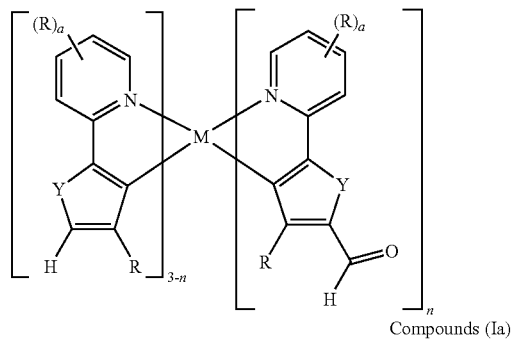
Compounds (II)

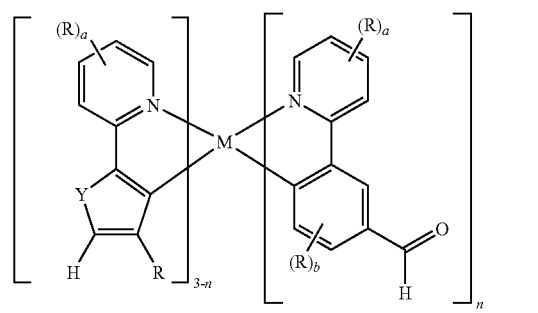
Compounds (Ia)

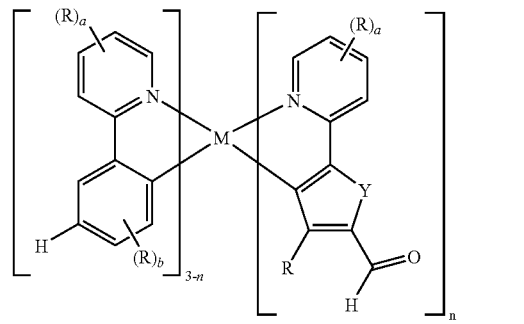
Compounds (IIa)

wherein

M is Rh or Ir;

Y is the same or different and is O, S, or Se;

R is the same or different on each occurrence and is H, F, Cl, Br, $NO_2$, CN, or a straight-chain or branched or cyclic alkyl or alkoxy group having 1 to 20 carbon atoms, wherein one or more non-adjacent $CH_2$ groups is optionally replaced by —O—, —S—, —NR¹—or —CONR² —and wherein one or more H atoms is optionally replaced by F, or an aryl or heteroaryl group having 4 to 14 carbon atoms which are optionally substituted by one or more non-aromatic radicals R;

$R^1$ and $R^2$ are each the same or different and are H or an aliphatic or aromatic hydrocarbon radical having 1 to 20 carbon atoms;

a is the same or different and is 0, 1, 2, 3, or 4;

b is the same or different and is 0, 1, 2, or 3; and n is 1, 2, or 3.

16. The method of claim 15, wherein the polymer is selected from the group consisting of polyfluorenes, polyspirobifluorenes, poly-para-phenylenes, poly-carbazoles, and polythiophenes.

17. The method of claim 15 wherein the polymer is a homo- or co-polymer.

18. The method of claim 15, wherein the polymer is soluble in organic solvents.

19. A method of manufacturing an electrical component comprising at least one conjugated or partially conjugated polymer, comprising the step of incorporating into a polymer a compound of formulas (I), (II), (Ia), or (IIa):

Compounds (I)

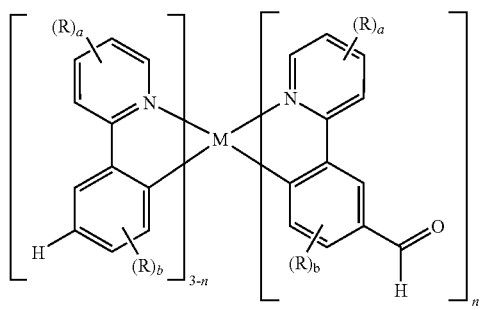

Compounds (II)

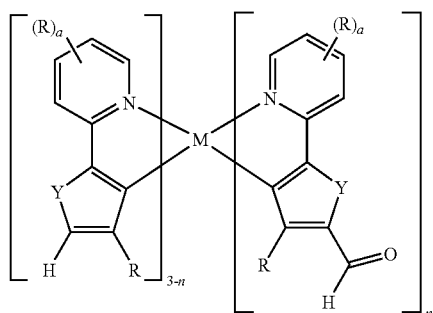

Compounds (Ia)

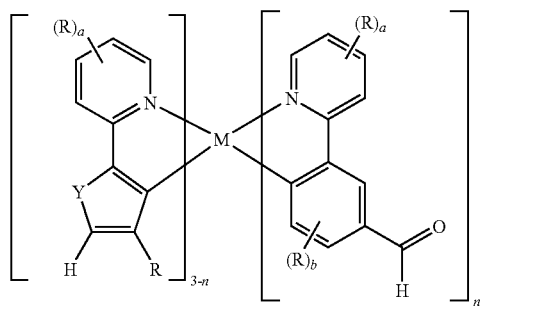

Compounds (IIa)

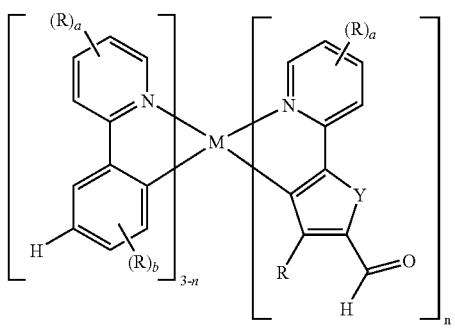

wherein

M is Rh or Ir;

Y is the same or different and is O, S, or Se;

R is the same or different on each occurrence and is H, F, Cl, Br, $NO_2$, CN, or a straight-chain or branched or cyclic alkyl or alkoxy group having 1 to 20 carbon atoms, wherein one or more non-adjacent $CH_2$ groups is optionally replaced by —O—, —S—, —$NR^1$— or —$CONR^2$— and wherein one or more H atoms is optionally replaced by F, or an aryl or heteroaryl group having 4 to 14 carbon atoms which are optionally substituted by one or more non-aromatic radicals R, $R^1$ and $R^2$ are each the same or different and are H or an aliphatic or aromatic hydrocarbon radical having 1 to 20 carbon atoms;

a is the same or different and is 0, 1, 2, 3, or 4;

b is the same or different and is 0, 1, 2, or 3; and n is 1, 2, or 3.

20. The method of claim 19, wherein the electrical component is an organic light emitting diode, an organic integrated circuit, an organic field effect transistor, an organic thin film transistor, an organic solar cell, an organic laser diode, an organic color filter for liquid crystal displays, or an organic photoreceptor.

* * * * *